United States Patent [19]

Absil et al.

[11] Patent Number: 5,013,422

[45] Date of Patent: * May 7, 1991

[54] CATALYTIC HYDROCRACKING PROCESS

[75] Inventors: Robert P. L. Absil, W. Deptford; Thomas F. Degnan, Moorestown; Scott Han, Lawrenceville; David O. Marler, Deptford, all of N.J.; Richard F. Socha, Newtown, Pa.; Michael R. Stapleton, Freehold, N.J.

[73] Assignee: Mobil Oil Corp., Fairfax, Va.

[*] Notice: The portion of the term of this patent subsequent to Nov. 6, 2007 has been disclaimed.

[21] Appl. No.: 479,790

[22] Filed: Feb. 14, 1990

Related U.S. Application Data

[63] Continuation-in-part of Ser. No. 254,524, Oct. 6, 1988, Pat. No. 4,954,325, which is a continuation-in-part of Ser. No. 98,176, Sep. 18, 1987, abandoned, which is a continuation-in-part of Ser. No. 890,268, Jul. 29, 1986, abandoned.

[51] Int. Cl.$^5$ ............... C10G 47/20; C10G 65/10
[52] U.S. Cl. .................................. 208/27; 208/18; 208/59; 208/111
[58] Field of Search ................. 208/111, 59, 18, 27

[56] References Cited

U.S. PATENT DOCUMENTS

| | | | |
|---|---|---|---|
| 3,140,249 | 7/1964 | Plank et al. | 208/120 |
| 3,140,251 | 7/1964 | Plank et al. | 208/120 |
| 3,140,252 | 7/1964 | Frilotte et al. | 208/120 |
| 3,140,253 | 7/1964 | Plank et al. | 208/120 |
| 3,271,418 | 9/1966 | Plank et al. | 208/120 |
| 3,535,225 | 10/1970 | Jaffe | 208/59 |
| 3,536,604 | 10/1970 | Jaffe | 208/59 |
| 3,536,605 | 10/1970 | Kittrell | 208/59 |
| 3,558,471 | 1/1971 | Kittrell | 208/59 |
| 3,617,498 | 11/1971 | Kittrell | 208/111 |
| 3,755,145 | 8/1973 | Orkin | 208/18 |
| 3,758,402 | 9/1973 | Oleck et al. | 208/111 |
| 3,788,974 | 1/1974 | Buchmann et al. | 208/59 |
| 3,894,930 | 7/1975 | Hensley, Jr. | 208/111 |
| 3,926,782 | 12/1975 | Plank et al. | 208/135 |
| 4,001,106 | 1/1977 | Plank et al. | 208/59 |
| 4,054,539 | 10/1977 | Hensley, Jr. | 208/111 |
| 4,439,409 | 3/1984 | Puppe et al. | 423/329 |
| 4,612,108 | 9/1986 | Angevine et al. | 208/59 |
| 4,648,958 | 3/1987 | Ward | 208/59 |
| 4,812,224 | 3/1989 | Miller | 208/111 |
| 4,826,667 | 5/1989 | Zones et al. | 423/277 |
| 4,857,169 | 8/1989 | Abdo | 208/89 |
| 4,875,991 | 10/1989 | Kukes et al. | 208/111 |
| 4,954,325 | 9/1990 | Rubin et al. | 502/64 |
| 4,968,402 | 11/1990 | Kirker et al. | 208/68 |

FOREIGN PATENT DOCUMENTS

| | | | |
|---|---|---|---|
| 0231860 | 8/1987 | European Pat. Off. | 502/64 |
| 0293032 | 11/1988 | European Pat. Off. | 502/64 |

Primary Examiner—Anthony McFarlane
Attorney, Agent, or Firm—Alexander J. McKillop; Charles J. Speciale; Dennis P. Santini

[57] ABSTRACT

A hydrocracking process is provided comprising contacting a hydrocarbon stream under hydrocracking conditions and in the presence of hydrogen with a catalyst composition which comprises a synthetic porous crystalline zeolite having a particular X-ray diffraction pattern. An embodiment of the invention provides a process for reducing the pour point of a waxy component-containing hydrocarbon oil by hydrocracking and dewaxing. Another embodiment of the invention provides a dual-stage hydrocracking process to produce premium gasoline and distillate boiling range products.

25 Claims, 2 Drawing Sheets

CATALYTIC HYDROCRACKING PROCESS

CROSS-REFERENCE TO RELATED APPLICATIONS

This application is a continuation-in-part of U.S. patent application Ser. No. 254,524, filed Oct. 6, 1988, now U.S. Pat. No. 4,954,325, which is a continuation-in-part of U.S. patent application Ser. No. 98,176, filed Sept. 18, 1987, now abandoned, which is a continuation-in-part of U.S. patent application Ser. No. 890,268, filed July 29, 1986, now abandoned.

BACKGROUND OF THE INVENTION

This invention relates to a catalytic hydrocracking process for upgrading hydrocarbon streams.

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties. Such molecular sieves, both natural and synthetic, include a wide variety of positive ion-containing crystalline silicates. These silicates can be described as a rigid three-dimensional framework of $SiO_4$ and Periodic Table Group IIIA element oxide, e.g. $AlO_4$, in which the tetrahedra are cross-linked by the sharing of oxygen atoms whereby the ratio of the total Group IIIA element, e.g. aluminum, and silicon atoms to oxygen atoms is 1:2. The electrovalence of the tetrahedra containing the Group IIIA element, e.g. aluminum, is balanced by the inclusion in the crystal of a cation, e.g. an alkali metal or an alkaline earth metal cation. This can be expressed wherein the ratio of the Group IIA element, e.g. aluminum, to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given silicate by suitable selection of the cation. The spaces between the tetrahedra are occupied by molecules of water prior to dehydration.

Prior art techniques have resulted in the formation of a great variety of synthetic zeolites. Many of these zeolites have come to be designated by letter or other convenient symbols, as illustrated by zeolite Z (U.S. Pat. No. 2,882,243); zeolite X (U.S. Pat. No. 2,882,244); zeolite Y (U.S. Pat. No. 3,130,007); zeolite ZK-5 (U.S. Pat. No. 3,247,195); zeolite ZK-4 (U.S. Pat. No. 3,314,752); zeolite ZSM-5 (U.S. Pat. No. 3,702,886); zeolite ZSM-11 (U.S. Pat. No. 3,709,979); zeolite ZSM-12 (U.S. Pat. No. 3,832,449); zeolite ZSM-20 (U.S. Pat. No. 3,972,983); zeolite ZSM-35 (U.S. Pat. No. 4,016,245); and zeolite ZSM-23 (U.S. Pat. No. 4,076,842), merely to name a few.

The $SiO_2/Al_2O_3$ ratio of a given zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the $SiO_2/Al_2O_3$ ratio is at least 5 and up to the limits of present analytical measurement techniques. U.S. Pat. No. 3,941,871 (U.S. Pat. No. Re. 29,948) discloses a porous crystalline silicate made from a reaction mixture containing no deliberately added alumina in the recipe and exhibiting the X-ray diffraction pattern characteristic of ZSM-5. U.S. Pat. Nos. 4,061,724; 4,073,865 and 4,104,294 describe crystalline silicates of varying alumina and metal content.

The hydrocracking of hydrocarbons to produce lower boiling hydrocarbons, and in particular, hydrocarbons boiling in the motor fuel range, is an operation upon which a vast amount of time and effort has been spent in view of its commercial significance. Hydrocracking catalysts usually comprise a hydrogenation-dehydrogenation component deposited on an acidic support such as silica-alumina, silica-magnesia, silica-zirconia, alumina, acid treated clays, zeolites, and the like.

Zeolites have been found to be particularly effective in the catalytic hydrocracking of a gas oil to produce motor fuels and such has been described in many U.S. patents including U.S. Pat. Nos. 3,140,249; 3,140,251; 3,140,252; 3,140,253; and, 3,271,418.

A catalytic hydrocracking process utilizing a catalyst comprising a zeolite dispersed in a matrix of other components such as nickel, tungsten and silica-alumina is described in U.S. Pat. No. 3,617,498.

A hydrocracking catalyst comprising a zeolite and a hydrogenation-dehydrogenation component such as nickel-tungsten sulfide is disclosed in U.S. Pat. No. 4,001,106.

The hydrocracking process described in U.S. Pat. No. 3,758,402 utilizes a catalyst possessing a large pore size zeolite component such as zeolite X or Y and an intermediate pore size zeolite component such as ZSM-5 with a hydrogenation-dehydrogenation component such as nickel-tungsten being associated with at least one of the zeolites.

Hydrocarbon conversion utilizing a catalyst comprising a zeolite, such as ZSM-5, having a zeolite particle diameter in the range of 0.005 micron to 0.1 micron and in some instances containing a hydrogenation-dehydrogenation component is disclosed in U.S. Pat. No. 3,926,782.

The hydrocracking of lube oil stocks employing a catalyst comprising a hydrogenation component and a zeolite such as ZSM-5 is disclosed in U.S. Pat. No. 3,755,145.

Hydrocracking operations featuring the use of dual reaction stages, or zones, and/or two different catalysts are also known.

U.S. Pat. No. 3,535,225 discloses a dual-catalyst hydrocracking process in which a hydrocarbon feedstock is initially contacted with a first catalyst comprising a hydrogenation component and a component selected from the group consisting of alumina and silica-alumina and subsequently with a second catalyst provided as a silica-based gel, a hydrogenation component and a zeolite in the ammonia or hydrogen form and free of any loading metal or metals.

U.S. Pat. No. 3,536,604 discloses a hydrofining-hydrocracking process in which a hydrocarbon feed containing 300 to 10,000 ppm organic nitrogen is contacted with a hydrofining catalyst comprising a Group VI or Group VIII metal on an alumina or silica-alumina support whereby the organic nitrogen content of the feed is reduced to a level of 10 ppm to 200 ppm, a substantial portion of the resulting hydrofined effluent thereafter being contacted with a second catalyst comprising a gel matrix comprising at least 15 wt. % silica, alumina, nickel and/or cobalt, molybdenum and/or tungsten, and a zeolite in the ammonia or hydrogen form and free of any loading metal.

U.S. Pat. No. 3,536,605 discloses a hydrofining-hydrocracking process in which a hydrocarbon feed containing substantial amounts of organic nitrogen is contacted in a hydrofining reaction zone under hydrofining conditions with a catalyst comprising a gel matrix comprising silica and alumina and nickel and/or cobalt and molybdenum and/or tungsten and a zeolite having a silica-to-alumina ratio above about 2.15, a unit cell size below about 24.65 Angstroms (A), and a sodium content below about 3 wt. % to produce a hydrofined product of reduced nitrogen content. The effluent from the hydrofining reaction zone is then hydrocracked in a hydrocracking reaction zone under hydrocracking conditions in the presence of hydrogen and a hydrocracking catalyst.

U.S. Pat. No. 3,558,471 discloses a two-catalyst process wherein a hydrocarbon feedstock is first hydrotreated in the presence of a catalyst comprising a silica-alumina gel matrix containing nickel or cobalt, or both, and molybdenum or tungsten, or both, and a zeolite substantially in the ammonia or hydrogen form free of any catalytic loading metal or metals, the zeolite having a silica-to-alumina ratio above about 2.15, unit cell size below about 24.65 A, and a sodium content belwo about 3 wt. %, calculated as $Na_2O$, to produce a first effluent which is thereafter hydrocracked in a second reaction zone in the presence of a hydrocracking catalyst which may be the same catalyst used in the first reaction zone or a conventional hydrocracking catalyst.

U.S. Pat. No. 3,788,974 discloses a two-catalyst hydrocracking process wherein a hydrocarbon oil feedstock containing from about 0.01 to 0.5 wt. % nitrogen compounds is contacted in a first hydrocracking zone with a zeolite catalyst of the faujasite type in combination with a nickel/tungsten hydrogenation component to provide an effluent which is contacted in a second separate hydrocracking zone with a hydrocracking catalyst, preferably zeolite X or Y.

In U.S. Pat. Nos. 3,894,930 and 4,054,539, a hydrocracking process is disclosed which employs a catalyst comprising a hydrogenation component, an ultrastable zeolite and a silica-alumina cracking catalyst.

U.S. Pat. No. 4,612,108 discloses a process in which an initial hydrotreating stage employing a conventional hydrotreating catalyst is followed by a hydrocracking stage employing zeolite Beta as the hydrocracking catalyst.

Catalytic hydrocracking of a hydrocarbon feedstock can in certain cases be accompanied by dewaxing, that is selective conversion of straight-chain and slightly branched paraffins, such that the pour point of the product is reduced. See U.S. Pat. No. 3,668,113.

It is known to produce a high quality lube base stock oil by subjecting a waxy crude oil fraction to solvent refining, followed by catalytic dewaxing over ZSM-5, with subsequent hydrotreating of the lube base stock as described in U.S. Pat. No. 4,181,598. Zeolites such as ZSM-5, ZSM-11, ZSM-12, ZSM-23, ZSM-35, and ZSM-38 have been proposed for dewaxing processes and their use is described in U.S. Pat. Nos. 3,894,938; 4,176,050; 4,181,598; 4,222,855; 4,229,282; and 4,247,388. A dewaxing process employing synthetic offretite is described in U.S. Pat. No. 4,259,174.

The use of zeolite Beta as catalyst for dewaxing hydrocarbon feedstocks such as distillate fuel oils by isomerization is described in U.S. Pat. Nos. 4,419,220 and 4,501,926. U.S. Pat. No. 4,486,296 teaches hydrodewaxing and hydrocracking of a hydrocarbon feedstock over a three-component catalyst including zeolite Beta. Dewaxing a paraffin-containing hydrocarbon feedstock employing a hydrotreating step prior to the dewaxing step over zeolite Beta catalyst is disclosed in U.S. Pat. Nos. 4,518,485 and 4,612,108. U.S. Pat. No. 4,481,104 discloses distillate-selective hydrocracking using a large pore, high silica, low acidity catalyst, e.g. zeolite Beta catalyst. Hydrocracking $C_5+$ naphthas over a catalyst comprising zeolite Beta is disclosed in U.S. Pat. No. 3,923,641. A dewaxing process using a noble metal/zeolite Beta catalyst followed by a base metal/zeolite Beta catalyst is disclosed in U.S. Pat. No. 4,554,065. U.S. Pat. No. 4,541,919 discloses a dewaxing process using a large pore zeolite catalyst such as zeolite Beta which has been selectively coked. U.S. Pat. No. 4,435,275 describes a moderate pressure hydrocracking process which may use a catalyst comprising zeolite Beta for producing low pour point distillates.

European patent application No. 94,827 discloses the use of zeolite Beta for hydrocracking and compares it for that process with other hydrocracking catalysts such as high silica zeolite Y, zeolite X and ZSM-20 (as described in European patent application No. 98,040). U.S. Pat. No. 4,612,108 describes the hydrocracking and dewaxing of waxy petroleum fractions by passing the fractions over a hydrocracking catalyst comprising zeolite Beta and a matrix material in the presence of hydrogen and under hydrocracking conditions, the proportion of zeolite Beta in the hydrocracking catalyst increasing in the direction in which the fraction is passed.

U.S. Pat. No. 4,601,993 describes the dewaxing of a lubricating oil feedstock by passing the waxy fraction over a catalyst bed containing a mixture of medium-pore size zeolite and large-pore zeolite having a Constraint Index of less than 2 and having hydroisomerization activity in the presence of a hydrogenation component.

U.S. Pat. No. 4,358,362 discloses a dewaxing process in which the feed is subjected to pretreatment with a zeolite sorbent to sorb zeolite poisons present therein.

It is known to produce lubricating oil of improved properties by hydrotreating the lubricating oil base stock in the presence of ZSM-39 containing cobalt and molybdenum, as shown in U.S. Pat. No. 4,395,327.

SUMMARY OF THE INVENTION

In accordance with the present invention, there is provided a hydrocracking process which comprises contacting a hydrocarbon stream under hydrocracking conditions and in the presence of hydrogen with a hydrocracking catalyst composition comprising a synthetic porous crystalline zeolite, hereafter referred to as "MCM-22", having an X-ray diffraction pattern including lines set forth in Table I, infra. A particular embodiment of the present invention provides a process for reducing the pour point of a waxy component-containing hyrocarbon oil feed which comprises contacting said feed with a catalyst composition under conditions suitable to effect hydrocracking and dewaxing of said feed to provide a hydrocracked/dewaxed product of reduced pour point, said catalyst composition comprising said synthetic porous crystalline material.

Another embodiment of the present invention provides a dual-stage hydrocracking process which comprises:

(a) contacting a hydrocarbon stream, for example one boiling above a temperature of about 300° F., in a first stage under hydrocracking conditions and in the presence of hydrogen with a first hydrocracking catalyst composition comprising said synthetic porous crystalline material and at least one hydrogenation component to provide a first hydrocracked effluent; and (b) contacting said first hydrocracked effluent in a second stage under hydrocracking conditions and in the presence of hydrogen with a second hydrocracking catalyst composition comprising (i) a molecular sieve having a larger pore size than the first stage catalyst, e.g. zeolite Beta, and (ii) at least one hydrogenation component to provide a second hydrocracked effluent.

The dual-stage hydrocracking process embodiment of this invention exploits the ability of the first hydrocracking catalyst composition to selectively convert aromatics present in the feedstock introduced to the first stage to paraffins and naphthenes and the ability of the second stage hydrocracking catalyst composition to selectively convert the paraffins to more highly isomerized products having lower pour points.

The terms "hydrocracking" and "hydrocracking conditions" shall be understood herein and in the appended claims to refer to any hydroconversion operation in which a relatively heavy hydrocarbon undergoes mild cracking to hydrocarbon products of lower molecular weight. These terms are to be regarded herein as inclusive not only of hydrocracking per se but such hydroconversion operations as paraffin isomerization.

DESCRIPTION OF SPECIFIC EMBODIMENTS

Figure 1:
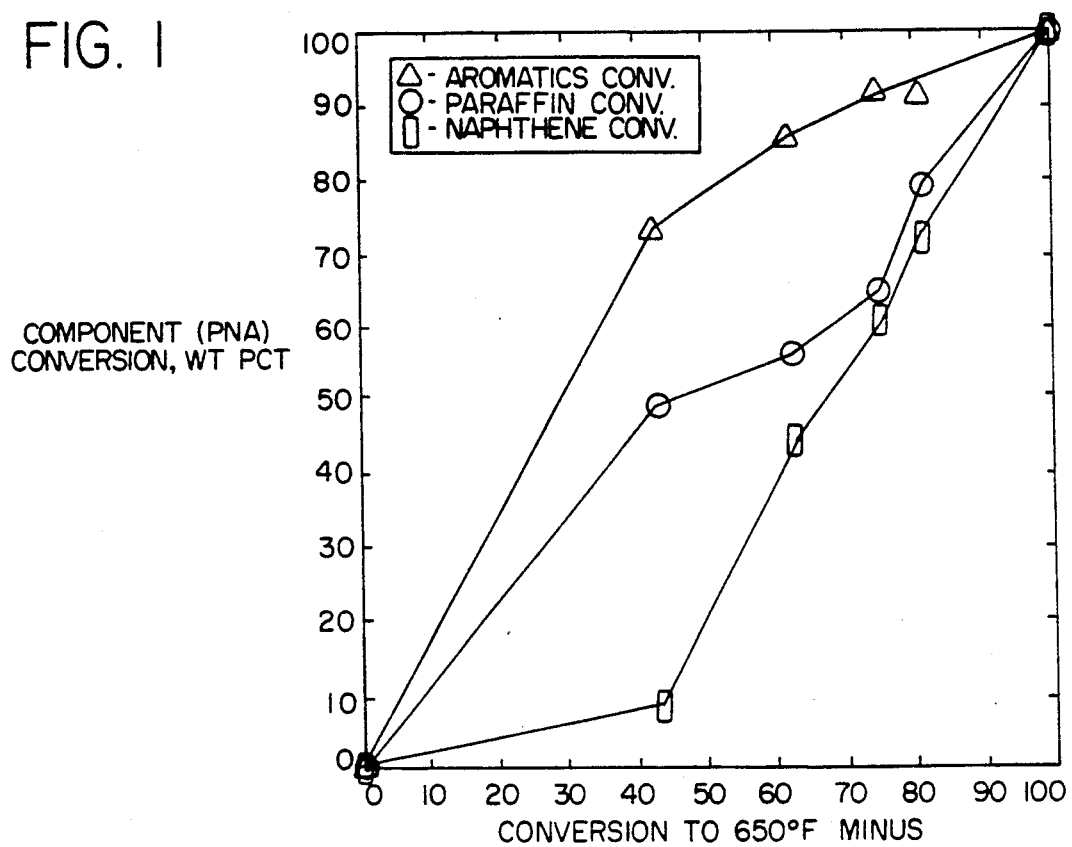
FIG. 1 is a graphical representation of process performance data relating to a catalytic hydrocracking process over NiW/MCM-22/Al$_2$O$_3$ catalyst.

The present process is especially advantageous for hydrocracking heavier waxy fractions, e.g. those having boiling points of 343° C. (650° F.) or higher, e.g. light virgin gas oils, light catalytic cycle oils and light vacuum gas oils, and their mixtures. The present process enables such heavy feedstocks to be converted to distillate range products boiling below 343° C. (650° F.); but in contrast to prior processes which use large-pore catalysts such as zeolite Y, the consumption of hydrogen is less and, for a given rate of conversion, product pour point is lower, that is, the hydrocracking is accompanied by dewaxing. In contrast to dewaxing processes using more shape selective catalysts, bulk conversion, including cracking of aromatic components, takes place, ensuring acceptably low viscosity in the distillate range product. Thus, the present process is capable of effecting bulk conversion together with simultaneous dewaxing. Moreover, this is achieved with a reduced hydrogen consumption as compared to other types of processes. It is also possible to operate at partial conversion, thus, effecting economies in hydrogen consumption while still meeting product pour point and viscosity requirements.

While not intending to be bound by theory, it is believed that during conversion, aromatics and naphthenes which are present in the feedstock undergo hydrocracking reactions such as dealkylation, ring opening and cracking, followed by hydrogenation. The long-chain normal and slightly-branched paraffins which are present in the feedstock, together with the paraffins produced by the hydrocracking of the aromatics are, in addition, converted into products which are less waxy than the straight-chain paraffins, thereby effecting simultaneous dewaxing. The process of the present invention produces not only a reduction in the viscosity of the original feed by hydrocracking but also a simultaneous reduction in its pour point by hydrodewaxing.

Suitable feedstocks for the present invention range from relatively light distillate fractions up to high boiling stocks such as whole crude petroleum, reduced crudes, vacuum tower residua, propane deasphalted residua, e.g. brightstock, cycle oils, FCC tower bottoms, gas oils, vacuum gas oils, deasphalted residua and other heavy oils. The feedstock will normally be a $C_{10}+$ feedstock, since light oils will usually be free of significant quantities of waxy components. However, the process is also particularly useful with waxy distillate stocks such as gas oils, kerosenes, jet fuels, lubricating oil stocks, heating oils, hydrotreated oil stock, furfural-extracted lubricating oil stock and other distillate fractions whose pour point and viscosity properties need to be maintained within certain specification limits. Lubricating oil stocks, for example, will generally boil above 230° C. (450° F.) and more usually above 315° C. (600° F.). For purposes of this invention, lubricating oil or lube oil is that part of hydrocarbon feedstock having a boiling point of 315° C. (600° F.) or higher, as determined by ASTM D-1160 test method.

The hydrocarbon feedstocks which can be treated by the hydrocracking process of the present invention will typically boil at a temperature above 150° C. (300° F.). Advantageously, the feedstocks will be those which boil within the range of 177° to 538° C. (350° F. to 1000° F.). The feedstocks can contain a substantial amount of nitrogen, e.g. at least 10 ppm nitrogen, and even greater than 500 ppm in the form of organic nitrogen compounds. The feeds can also have a significant sulfur content, ranging from 0.1 wt. % to 3 wt. %, or higher. If desired, the feeds can be treated in a known or conventional manner to reduce the sulfur and/or nitrogen content thereof.

Conveniently, the hydrocracking process of the invention also includes the step of contacting the hydrocarbon feed, either in the same or a separate stage, with a second catalyst composition comprising (i) a molecular sieve having a larger pore size than the zeolite of Table I, e.g. zeolite beta, and (ii) at least one hydrogenation component. Such a two-catalyst scheme exploits the ability of the hydrocracking catalyst composition of the invention to selectively convert aromatics present in the feedstock to paraffins and naphthenes and the ability of the second hydrocracking catalyst composition to selectively convert the paraffins in the first stage effluent to more highly isomerized products having lower pour points.

The feedstocks to be treated by the two-catalyst hydrocracking embodiment of the present invention will ordinarily contain a substantial amount of cyclic hydrocarbons, i.e. aromatic and/or naphthenic hydrocarbons. Advantageously, the feeds can contain 3 wt. % to 40 wt. % aromatics and/or naphthenes. Examples of hydrocarbon streams which can be treated by the two-stage hydrocracking embodiment are light vacuum gas oils, heavy vacuum gas oils, light catalytic cycle oils, heavy catalytic cycle oils, virgin gas oils, and mixtures thereof.

In its calcined form, the zeolite employed in the hydrocracking catalyst composition of the invention has an X-ray diffraction pattern which includes the lines listed in Table I below:

TABLE I

| Interplanar d-Spacing (A) | Relative Intensity, I/Io × 100 |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

More specifically, the calcined form may be characterized by an X-ray diffraction pattern including the following lines:

TABLE II

| Interplanar d-Spacing (A) | Relative Intensity, I/Io × 100 |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 I/I$_o$, where I$_o$ is the intensity of the strongest line or peak, and d (obs.) the interplanar spacing in Angstroms Units (A), corresponding to the recorded lines, were determined. In Table I, the relative intensities are given in terms of the symbols W=weak, M=medium, S=strong and VS=very strong. In terms of intensities, these may be generally designated as follows:

W=0–20

M=20–40

S=40–60

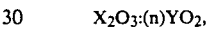=60–100.

It should be understood that these X-ray diffraction patterns are characteristic of all species of the present zeolite. The sodium form as well as other cationic forms reveal substantially the same pattern with some minor shifts in interplanar spacing and variation in relative intensity. Other minor variations can occur depending on the Y to X, e.g. silicon to aluminum, mole ratio of the particular sample, as well as its degree of thermal treatment.

The synthetic porous crystalline zeolite employed in the hydrocracking catalyst composition of the invention has a composition involving the molar relationship:

$$X_2O_3:(n)YO_2,$$

wherein X is a trivalent element, such as aluminum, boron, iron and/or gallium, preferably aluminum, Y is a tetravalent element such as silicon and/or germanium, preferably silicon, and n is at least 10, usually from 10 to 150, more usually from 10 to 60, and even more usually from 20 to 40. In the as-synthesized form, the zeolite has a formula, on a anhydrous basis and in terms of moles of oxides per n moles of YO$_2$, as follows:

wherein R is an organic component. The Na and R components are associated with the zeolite as a result of their presence during crystallization, and are easily removed by post-crystallization methods hereinafter more particularly described.

The above zeolite is thermally stable and exhibits high surface area greater than 400 m$^2$/gm as measured by the BET (Bruenauer, Emmet and Teller) test and unusually large sorption capacity when compared to similar crystal structures. In particular the zeolite exhibits equilibrium adsorption values greater than 4.5 wt. % for cyclohexane vapor and greater than 10 wt. % for n-hexane vapor. As is evident from the above formula, the zeolite is synthesized nearly free of Na cations. It can, therefore, be used as a hydrocracking catalyst with acid activity without an exchange step. To the extent desired, however, the original sodium cations of the as-synthesized material can be replaced in accordance with techniques well known in the art, at least in part, by ion exchange with other cations. Preferred replacing cations include metal ions, hydrogen ions, hydrogen precursor, e.g. ammonium, ions and mixtures thereof. Particularly preferred cations are those which tailor its catalytic activity for hydrocracking reactions. These include hydrogen, rare earth metals and metals of Groups IIA, IIIA, IVA, IB, IIB, IIIB, IVB and VIII of the Periodic Table of the Elements.

Prior to its use in a hydrocracking catalyst composition, the present zeolite crystals should be subjected to thermal treatment to remove part or all of any organic constituent present therein.

Prior to use, the present zeolite should be dehydrated, at least partially. This can be done by heating the crystals to a temperature in the range of 200° C. to 595° C. in an inert atmosphere, such as air and nitrogen, and at atmospheric, subatmospheric or superatmospheric pressures for between 30 minutes and 48 hours. Dehydration can also be performed at room temperature merely by placing the crystalline material in a vacuum, but a longer time is required to obtain a sufficient amount of dehydration.

The zeolite employed in the present invention can be prepared from a reaction mixture containing sources of alkali or alkaline earth metal (M), e.g. sodium or potassium, cation, an oxide of trivalent element X, e.g aluminum, an oxide of tetravalent element Y, e.g. silicon, an organic (R) directing agent, hexamethyleneimine, and water, said reaction mixture having a composition, in terms of mole ratios of oxides, within the following ranges:

| Reactants | Useful | Preferred |
|---|---|---|
| $YO_2/X_2O_3$ | 10–60 | 10–40 |
| $H_2O/YO_2$ | 5–100 | 10–50 |
| $OH^-/YO_2$ | 0.01–1.0 | 0.1–0.5 |
| $M/YO_2$ | 0.01–2.0 | 0.1–1.0 |
| $R/YO_2$ | 0.05–1.0 | 0.1–0.5 |

In a preferred synthesis method, the $YO_2$ reactant contains a substantial amount of solid $YO_2$, e.g. at least 30 wt. % solid $YO_2$. Where $YO_2$ is silica, the use of a silica source containing at least 30 wt. % solid silica, e.g. Ultrasil (a precipitated, spray dried silica containing 90 wt. % silica) or HiSil (a precipitated hydrated $SiO_2$ containing 87 wt. % silica, 6 wt. % free $H_2O$ and 4.5 wt. % bound $H_2O$ of hydration and having a particle size of 0.02 micron) favors crystal formation from the above mixture. If another source of oxide of silicon, e.g. Q-Brand (a sodium silicate comprised of 28.8 wt. % of $SiO_2$, 8.9 wt. % $Na_2O$ and 62.3 wt. % $H_2O$) is used, crystallization may yield little or none of the desired crystalline material. Impurity phases of other crystal structures, e.g. ZSM-12, are prepared in the latter circumstance. Preferably, therefore, the $YO_2$, e.g. silica, source contains at least 30 wt. % solid $YO_2$, e.g. silica, and more preferably at least 40 wt. % solid $YO_2$ e.g., silica.

Crystallization can be carried out at either static or stirred conditions in a suitable reactor vessel such as, e.g. polypropylene jars or teflon lined or stainless steel autoclaves. Generally crystallization is conducted at a temperature of 80° C. to 225° C. for 25 hours to 60 days. Thereafter, the crystals are separated from the liquid and recovered.

Crystallization is facilitated by the presence in the reaction mixture of at least 0.01 percent, preferably 0.10 percent and still more preferably 1 percent, seed crystals (based on total weight) of the crystalline product.

Prior to use in the process of the invention, it may be desirable to incorporate the zeolite described above with another material, or matrix, which is resistant to the temperatures and other conditions employed in the process. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the zeolite, i.e. combined therewith or present during its synthesis, which itself is catalytically active may change the conversion and/or selectivity of the catalyst. Inactive materials suitably serve as diluents to control the amount of conversion so that hydrocracked products can be obtained economically and orderly without employing other means for controlling the rate of reaction. These materials may be incorporated into naturally occurring clays, e.g. bentonite and kaolin, to improve the crush strength of the catalyst under commercial hydrocracking conditions. Said materials, i.e. clays, oxides, etc., function as binders for the catalyst. It is desirable to provide a catalyst having good crush strength because in commercial use, it is desirable to prevent the catalyst from breaking down into powder-like materials. These clay binders have been employed normally only for the purpose of improving the crush strength of the catalyst.

Naturally occurring clays which can be composited with the present zeolite include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the zeolite also include inorganic oxides, notably alumina.

In addition to the foregoing materials, the zeolite can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. It may also be advantageous to provide at least a part of the foregoing matrix materials in colloidal form so as to facilitate extrusion of the bound catalyst component(s).

The relative proportions of zeolite and inorganic oxide matrix vary widely, with the crystal content ranging from 1 to 90 percent by weight and, more usually, particularly when the composite is prepared in the form of beads, in the range 2 to 80 weight percent of the composite.

The hydrocracking catalyst composition also contains a hydrogenation component such as one or more of tungsten, vanadium, molybdenum, rhenium, nickel, cobalt, chromium, manganese, or one or more noble metals such as platinum, palladium where a hydrogenation-dehydrogenation function is to be performed. Such component can be introduced in the catalyst composition by way of co-crystallization, exchanged into the composition to the extent a Group IIA element, e.g. aluminum, is in the structure, impregnated therein or intimately physically admixed therewith. Such component can be impregnated in or on the zeolite such as, for example, by, in the case of platinum, treating the zeolite with a solution containing a platinum metal-containing ion. Thus, suitable platinum compounds for this purpose include chloroplatinic acid, platinous chloride and various compounds containing the platinum amine complex.

The stability of hydrocracking catalyst of the invention may be increased by steaming which is conveniently effected by contacting the zeolite with, for example, 5-100% steam at a temperature of at least 300° C. (preferably 300°-650° C.) for at least one hour (preferably 1-200 hours) at a pressure of 101-2,500 kPa. In a more particular embodiment, the catalyst can be made to undergo steaming with 75-100% steam at 315°-500° C. and atmospheric pressure for 2-25 hours.

In general, the hydrocracking process of the invention is conducted at a temperature of 260° C. to 450° C., a pressure of 2860 to 27,680 kPa (400 to 4000 psig), a liquid hourly space velocity (LHSV) of 0.1 hr$^{-1}$ to 10 hr$^{-1}$ and a hydrogen circulation rate of 180 to 1780 Nm$^3$/m$^3$ (1000 to 10,000 standard cubic feet per barrel).

As previously stated, the hydrocracking process of the invention may also include the step of contacting the hydrocarbon feed, either in the same or a separate stage, with a second hydrocracking catalyst composition containing a molecular sieve, such as a zeolite Beta, which has a larger pore size than the zeolite of Table I and (ii) a hydrogenation component such as any of those previously mentioned. Zeolite Beta is described in U.S. Reissue No. 28,341 (of original U.S. Pat. No. 3,308,069) and may be combined with one or more other matrix materials which are resistant to the process conditions, e.g. any of the matrix materials previously identified herein. Where the zeolite beta composition contacts the feed in a separate hydrocracking stage, this is conveniently effected by passing the effluent from a first stage employing the zeolite of Table I, without prior separation of lighter products, over the zeolite Beta composition. The latter operates under hydrocracking conditions which are within the foregoing ranges and effects selective isomerization of paraffinic components in the first stage effluent. Where the feed is subjected to a single hydrocracking stage, the zeolite of Table I may be composited with the zeolite Beta into a single catalyst particle or may be used as a separate particulate catalyst.

Where the feedstock to be hydrocracked according to the process of the invention contains significant quantities of nitrogen and/or sulfur, it may be desirable initially to subject the feedstock to a conventional hydrotreating process. Hydrotreating can be conducted at low to moderate pressures, typically from 3000 kPa to 10,000 kPa, with the temperature maintained at 350° C. to 450° C. Hydrotreating catalysts include those relatively immune to poisoning by the nitrogenous and sulfurous impurities in the feedstock and generally comprise a non-noble metal component supported on an amorphous, porous carrier such as silica, alumina, silica-alumina or silica-magnesia. Other support materials such as zeolite Y or other large-pore zeolites, either alone or in combination with binders such as silica, alumina, or silica-alumina, can also be used for this purpose. Because extensive cracking is not desired in the hydrotreating operation, the acidic functionality of the carrier can be relatively low compared to that of the hydrocracking/dewaxing catalyst described below. The metal component can be a single metal from Groups VIB and VIII of the Periodic Table such as nickel, cobalt, chromium, vanadium, molybdenum, tungsten, or a combination of metals such as nickel-molybdenum, cobalt-nickel, molybdenum, cobalt-molybdenum, nickel-tungsten or nickel-tungsten-titanium. Generally, the metal component will be selected for good hydrogen transfer activity. The catalyst as a whole will have a good hydrogen transfer activity and minimal cracking characteristics. The catalyst should be pre-sulfided in the normal way in order to convert the metal component (usually impregnated into the carrier and converted to oxide) to the corresponding sulfide.

In the hydrotreating operation, nitrogen and sulfur impurities are converted to ammonia and hydrogen sulfide, respectively. At the same time, polycyclic aromatics are more readily cracked in the present process to form alkyl aromatics. The effluent from the hydrotreating step can be passed directly to the present process without conventional interstage separation of ammonia or hydrogen sulfide although hydrogen quenching can be carried out in order to control the effluent temperature and to control the catalyst temperature in the present process. However, if desired, interstage separation of ammonia and hydrogen sulfide may be carried out.

In order to more fully illustrate the present invention, including the embodiments of hydrocracking/dewaxing and dual-stage hydrocracking and the manner of practicing same, the following examples are presented. In examples illustrative of the synthesis of zeolite MCM-22, whenever sorption data are set forth for comparison of sorptive capacities for water, cyclohexane and/or n-hexane, they were Equilibrium Adsorption values determined as follows:

A weighed sample of the calcined adsorbent was contacted with the desired pure adsorbate vapor in an adsorption chamber, evacuated to less than 1 mm Hg and contacted with 12 Torr of water vapor or 40 Torr of n-hexane or 40 Torr of cyclohexane vapor, pressures less than the vapor-liquid equilibrium pressure of the respective adsorbate at 90° C. The pressure was kept constant (within about ±0.5 mm Hg) by addition of adsorbate vapor controlled by a manostat during the adsorption perid, which did not exceed about 8 hours. As adsorbate was adsorbed by the MCM-22 crystalline material, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample in g/100 g of calcined adsorbant. Zeolite MCM-22 always exhibits Equilibrium Adsorption values of greater than about 10 wt. % for water vapor, greater than about 4.5 wt. %, usually greater than about 7 wt. % for cyclohexane vapor and greater than about 10 wt. % for n-hexane vapor. These vapor sorption capacities are a notable distinguishing feature of zeolite MCM-22.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant=0.016 sec$^{-1}$). The Alpha Test is described in U.S. Pat. No. 3,354,078, in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

EXAMPLE 1

One part of sodium aluminate (43.5% $Al_2O_3$, 32.2% $Na_2O$, 25.6% $H_2O$) was dissolved in a solution containing 1 part of 50% NaOH solution and 103.13 parts $H_2O$. To this was added 4.50 parts hexamethyleneimine. The resulting solution was added to 8.55 parts of Ultrasil, a precipitated, spray-dried silica (about 90% $SiO_2$).

The reaction mixture had the following composition, in mole ratios:

| | |
|---|---|
| $SiO_2/Al_2O_3 =$ | 30.0 |
| $OH^-/SiO_2 =$ | 0.18 |
| $H_2O/SiO_2 =$ | 44.9 |
| $Na/SiO_2 =$ | 0.18 |
| $R/SiO_2 =$ | 0.35 | where R is hexamethyleneimine.

The mixture was crystallized in a stainless steel reactor, with stirring, at 150° C. for 7 days to produce the MCM-22 zeolite of the invention. The crystalline product was filtered, washed with water and dried at 120° C. After a 20 hour calcination at 538° C., the X-ray diffraction pattern contained the major lines listed in Table III. The sorption capacities of the calcined material were measured to be:

| | |
|---|---|
| $H_2O$ | 15.2 wt. % |
| Cyclohexane | 14.6 wt. % |
| n-Hexane | 16.7 wt. % |

The surface area of the calcined crystalline material was measured to be $494^2$/g.

The chemical composition of the uncalcined material was determined to be as follows:

| Component | wt. % |
|---|---|
| $SiO_2$ | 66.9 |
| $Al_2O_3$ | 5.40 |
| Na | 0.03 |
| N | 2.27 |
| Ash | 76.3 |
| $SiO_2/Al_2O_3$, mole ratio = | 21.1 |

TABLE III

| Degrees 2-Theta | Interplanar d-Spacing (A) | $I/I_o$ |
|---|---|---|
| 2.80 | 31.55 | 25 |
| 4.02 | 21.98 | 10 |
| 7.10 | 12.45 | 96 |
| 7.95 | 11.12 | 47 |
| 10.00 | 8.85 | 51 |
| 12.90 | 6.86 | 11 |
| 14.34 | 6.18 | 42 |
| 14.72 | 6.02 | 15 |
| 15.90 | 5.57 | 20 |
| 17.81 | 4.98 | 5 |
| 20.20 | 4.40 | 20 |
| 20.91 | 4.25 | 5 |
| 21.59 | 4.12 | 20 |
| 21.92 | 4.06 | 13 |
| 22.67 | 3.92 | 30 |
| 23.70 | 3.75 | 13 |
| 24.97 | 3.57 | 15 |
| 25.01 | 3.56 | 20 |
| 26.00 | 3.43 | 100 |
| 26.69 | 3.31 | 14 |
| 27.75 | 3.21 | 15 |
| 28.52 | 3.13 | 10 |
| 29.01 | 3.08 | 5 |
| 29.71 | 3.01 | 5 |
| 31.61 | 2.830 | 5 |
| 32.21 | 2.779 | 5 |
| 33.35 | 2.687 | 5 |
| 34.61 | 2.592 | 5 |

EXAMPLE 2

A portion of the calcined crystalline product of Example 1 was tested in the Alpha Test and was found to have an Alpha Value of 224.

EXAMPLES 3-5

Three separate synthesis reaction mixtures were prepared with compositions indicated in Table IV. The mixtures were prepared with sodium aluminate, sodium hydroxide, Ultrasil, hexamethyleneimine (R) and water. The mixtures were maintained at 150° C., 143° C. and 150° C., respectively, for 7, 8 and 6 days respectively in stainless steel autoclaves at autogenous pressure. Solids were separated from any unreacted components by filtration and then water washed, followed by drying at 120° C. The product MCM-22 crystals were subjected to X-ray diffraction, sorption, surface area and chemical analyses. The results of sorption, surface area and chemical analyses are also presented in Table IV. The sorption and surface area measurements were of the calcined product.

TABLE IV

| Example | 3 | 4 | 5 |
|---|---|---|---|
| Synthesis Mixture, mole ratios | | | |
| $SiO_2/Al_2O_3$ | 30.0 | 30.0 | 30.0 |
| $OH^-/SiO_2$ | 0.18 | 0.18 | 0.18 |
| $H_2O/SiO_2$ | 19.4 | 19.4 | 44.9 |
| $Na/SiO_2$ | 0.18 | 0.18 | 0.18 |
| $R/SiO_2$ | 0.35 | 0.35 | 0.35 |
| Product Composition, Wt. % | | | |
| $SiO_2$ | 64.3 | 68.5 | 74.5 |
| $Al_2O_3$ | 4.85 | 5.58 | 4.87 |
| Na | 0.08 | 0.05 | 0.01 |
| N | 2.40 | 2.33 | 2.12 |
| Ash | 77.1 | 77.3 | 78.2 |
| $SiO_2/Al_2O_3$, mole ratio | 22.5 | 20.9 | 26.0 |
| Adsorption, Wt. % | | | |
| $H_2O$ | 14.9 | 13.6 | 14.6 |
| Cyclohexane | 12.5 | 12.2 | 13.6 |
| n-Hexane | 14.6 | 16.2 | 19.0 |
| Surface Area, m²/g | 481 | 492 | 487 |

EXAMPLE 6

Quantities of the calcined (538° C. for 3 hours) crystalline silicate products of Examples 3, 4 and 5 were tested in the Alpha Test and found to have Alpha Values of 227, 180 and 187, respectively.

EXAMPLE 7

To demonstrate a further preparation of the present zeolite, 4.49 parts of hexamethyleneimine was added to a solution containing 1 part of sodium aluminate, 1 part of 50% NaOH solution and 44.19 parts of $H_2O$. To the combined solution were added 8.54 parts of Ultrasil silica. The mixture was crystallized with agitation at 145° C. for 59 hours and the resultant product was water washed and dried at 120° C.

Product chemical composition, surface area and adsorption analyses results were set forth in Table V:

TABLE V

| Product Composition (uncalcined) | |
|---|---|
| C | 12.1 wt. % |
| N | 1.98 wt. % |
| Na | 640 ppm |
| $Al_2O_3$ | 5.0 wt.% |
| $SiO_2$ | 74.9 wt. % |
| $SiO_2/Al_2O_3$, mole ratio | 25.4 |
| Adsorption, wt. % | |
| Cyclohexane | 9.1 |
| N-Hexane | 14.9 |
| $H_2O$ | 16.8 |
| Surface Area, $m^2/g$ | 479 |

EXAMPLE 8

Twenty-five grams of solid crystal product from Example 7 were calcined in a flowing nitrogen atmospheres at 538° C. for 5 hours, followed by purging with 5% oxygen gas (balance $N_2$) for another 16 hours at 538° C.

Individual 3 g samples of the calcined material were ion-exchanged with 100 ml of 0.1N TEABr, TPABr and $LaCl_3$ solution separately. Each exchange was carried out at ambient temperature for 24 hours and repeated three times. The exchanged samples were collected by filtration, water-washed to be halide-free and dried. The compositions of the exchanged samples are tabulated below demonstrating the exchange capacity of the present crystalline silicate for different ions.

| Exchange Ions Ionic Composition, wt. % | TEA | TPA | La |
|---|---|---|---|
| Na | 0.095 | 0.089 | 0.063 |
| N | 0.30 | 0.38 | 0.03 |
| C | 2.89 | 3.63 | — |
| La | — | — | 1.04 |

EXAMPLE 9

The La-exchanged sample from Example 8 was sized to 14 to 25 mesh and then calcined in air at 538° C. for 3 hours. The calcined material had an Alpha Value of 173.

EXAMPLE 10

The calcined sample La-exchanged material from Example 9 was severely steamed at 649° C. in 100% steam for 2 hours. The steamed sample had an Alpha Value of 22, demonstrating that the zeolite had very good stability under severe hydrothermal treatment.

EXAMPLE 11

This example illustrates the preparation of the present zeolite where X in the general formula, supra, is boron. Boric acid, 2.59 parts, was added to a solution containing 1 part of 45% KOH solution and 42.96 parts $H_2O$. To this was added 8.56 parts of Ultrasil silica, and the mixture was thoroughly homogenized. A 3.88 parts quantity of hexamethyleneimine was added to the mixture. The reaction mixture had the following composition in mole ratios:

| $SiO_2/B_2O_3 =$ | 6.1 |
|---|---|
| $OH^-/SiO_2 =$ | 0.06 |
| $H_2O/SiO_2 =$ | 19.0 |
| $K/SiO_2 =$ | 0.06 |
| $R/SiO_2 =$ | 0.30 | where R is hexamethyleneimine.

The mixture was crystallized in a stainless steel reactor, with agitation, at 150° C. for 8 days. The crystalline product was filtered, washed with water and dried at 120° C. A portion of the product was calcined for 6 hours at 540° C. and found to have the following sorption capacities:

| $H_2O$ | 11.7 wt. % |
|---|---|
| Cyclohexane | 7.5 wt. % |
| n-Hexane | 11.4 wt. % |

The surface area of the calcined crystalline material was measured (BET) to be 405 $m^2/g$.

The chemical composition of the uncalcined material was determined to be as follows:

| N | 1.94 wt. % |
|---|---|
| Na | 175 ppm |
| K | 0.60 wt. % |
| Boron | 1.04 wt. % |
| $Al_2O_3$ | 920 ppm |
| $SiO_2$ | 75.9 wt. % |
| Ash | 74.11 wt. % |
| $SiO_2/Al_2O_3$, molar ratio = | 1406 |
| $SiO_2/(Al + B)_2O_3$, molar ratio = | 25.8 |

EXAMPLE 12

A portion of the calcined crystalline product of Example 11 was treated with $NH_4Cl$ and again calcined. The final crystalline product was tested in the Alpha Test and found to have an Alpha Value of 1.

EXAMPLE 13

This example illustrates another preparation of the zeolite in which X of the general formula, supra, is boron. Boric acid, 2.23 parts, was added to a solution of 1 part of 50% NaOH solution and 73.89 parts $H_2O$. To this solution was added 15.29 parts of HiSil silica followed by 6.69 parts of hexamethyleneimine. The reaction mixture had the following composition in mole ratios:

| $SiO_2/B_2O_2 =$ | 12.3 |
|---|---|
| $OH^-/SiO_2 =$ | 0.056 |
| $H_2O/SiO_2 =$ | 18.6 |
| $K/SiO_2 =$ | 0.056 |
| $R/SiO_2 =$ | 0.30 | where R is hexamethyleneimine.

The mixture was crystallized in a stainless steel reactor, with agitation, at 300° C. for 9 days. The crystalline product was filtered, washed with water and dried at 120° C. The sorption capacities of the calcined material (6 hours at 540° C.) were measured:

| $H_2O$ | 14.4 wt. % |
|---|---|
| Cyclohexane | 4.6 wt. % |

| | |
|---|---|
| n-Hexane | 14.0 wt. % |

The surface area of the calcined crystalline material was measured to be 438 m²/g.

The chemical compostion of the uncalcined material was determined to be as follows:

| Component | Wt. % |
|---|---|
| N | 2.48 |
| Na | 0.06 |
| Boron | 0.83 |
| Al$_2$O$_3$ | 0.50 |
| SiO$_2$ | 73.4 |
| SiO$_2$/Al$_2$O$_3$, molar ratio = | 249 |
| SiO$_2$/(Al + B)$_2$O$_3$, molar ratio = | 28.2 |

EXAMPLE 14

A portion of the calcined crystalline product of Example 13 was tested in the Alpha Test and found to have an Alpha Value of 5.

EXAMPLE 15

This example illustrates the preparation of NiW/MCM-22/Al$_2$O$_3$ catalyst which provides the first hydrocracking catalyst composition employed in the hydrocracking process illustrated in Example 17, infra.

The zeolite component of the first hydrocracking catalyst composition was synthesized by adding 4.49 parts quantity of hexamethyleneimine to a mixture containing 1.00 part sodium aluminate, 1.00 part 50% NaOH, 8.54 parts Ultrasil VN3 and 44.19 parts deionized H$_2$O. The reaction mixture was heated to 143° C. (290° F.) and stirred in an autoclave at that temperature for crystallization. After full crystallinity was achieved, the majority of the hexamethyleneimine was removed from the autoclave by controlled distillation and the zeolite crystals separated from the remaining liquid by filtration, washed with deionized water and dried. The product had an X-ray pattern including the lines of Tables I and II.

A portion of the zeolite crystals was combined with Al$_2$O$_3$ to form a mixture of 65 parts, by weight, zeolite and 35 parts Al$_2$O$_3$. Water was added to this mixture to allow the resulting catalysts to be formed into extrudates. The catalyst was activated by calcining at 480° C. (900° F.) in 3v/v/min, nitrogen for three hours, then treated with 50 vol. % air/50 vol % N$_2$ at 3v/v/min, also at 480° C. (900° F.) for 1 hour. The calcination was completed by raising the temperature to 540° C. (1000° F.) at 3° C./min and finally switching to 100% air (3v/v/min) and holding at 540° C. (1000° F.) for three hours. The calcined catalyst had an alpha value of 213. This material was then steamed at 480° C. (900° F.) in 100% steam to 12 hours. The resulting catalyst had an alpha value of 35.

The steamed extrudate was impregnated with ammonium metatungstate via a known and conventional incipient wetness technique at room temperature, dried overnight at 120° C. (250° F.), calcined in dry air at 1° C. (1.8° F.)/min to 540° C. (1000° F.) and held at this temperature in flowing air for three hours.

The tungsten-containing catalyst was then impregnated via the incipient wetness technique with nickel nitrate, dried overnight at 120° C. (250° F.), and then calcined in air using the previously described procedure. The finished NiW/zeolite/Al$_2$O$_3$ catalyst had the properties shown in Table VI as follows:

TABLE VI

Properties of NiW/zeolite/Al$_2$O$_3$ First Hydrocracking Catalyst Composition

| Density, g/cm³ | |
|---|---|
| Packed | 0.48 |
| Particle | 0.82 |
| Real | 2.57 |
| Pore Volume, cm³/g | 0.83 |
| Surface Area, m²/g | 451 |
| Pore Diameter, Angstroms | 74 |
| Alpha after Steaming | 35 |
| Sodium, ppm | 132 |
| Nickel, wt. % | 3.12 |
| Tungsten, wt. % | 7.85 |

EXAMPLE 16

This example illustrates the preparation of NiW/zeolite Beta/Al$_2$O$_3$ used to provide the second hydrocracking catalyst composition employed in the hydrocracking process illustrated in Example 17, infra.

The zeolite Beta component of the second hydrocracking catalyst composition was synthesized substantially as described in U.S. Pat. No. Re. 28,341 (of original U.S. Pat. No. 3,308,069). The zeolite was then ammonium exchanged twice at room temperature with 5 ml/g 1N ammonium nitrate. A 65 wt. % zeolite Beta/35 wt. % Al$_2$O$_3$ catalyst composition was prepared from this zeolite by extrusion. The material was dried overnight at 120° C. (250° F.), calcined at 540° C. (1000° F.) in 3 v/v/min N$_2$ at a heating rate of 5° F./min, held at 540° C. (1000° F.) for three hours in 3 v/v/min N$_2$, then treated with air for three hours at 3 v/v/min also at 540° C. (1000° F.). The calcined catalyst had an alpha of 380. This material was then steamed at 540° C. (1000° F.) in 100% steam 10 hours.

The steamed extrudate was impregnated with ammonium metatungstate via the incipient wetness technique at room temperature, dried overnight at 120° C. (250° F.), calcined in dry air at 1° C. (1.8° F.)/min to 540° C. (1000° F.) and held at this temperature in flowing air for three hours.

The tungsten containing catalyst was then impregnated via the incipient wetness technique with nickel nitrate, dried overnight at 120° C. (250° F.), and then calcined in air using the same procedure described above. The finished NiW/zeolite Beta/Al$_2$O$_3$ catalyst had the properties shown in Table VII as follows:

TABLE VII

Properties of NiW/zeolite Beta/Al$_2$O$_3$ Second Hydrocracking Catalyst Composition

| Density, g/cm³ | |
|---|---|
| Packed | 0.54 |
| Particle | 0.96 |
| Real | 2.64 |
| Pore Volume, cm³/g | 0.67 |
| Surface Area, m²/g | 384 |
| Pore Diameter, Angstroms | 69 |
| Alpha after Steaming | 52 |
| Sodium, ppm | 105 |
| Nickel, wt. % | 3.29 |
| Tungsten, wt. % | 7.39 |

EXAMPLE 17

Both the first and second hydrocracking catalyst compositions (Examples 15 and 16, respectively) were individually compared for their activity and selectivity in converting a vacuum gas oil (VGO) having the properties shown in Table VIII as follows:

TABLE VIII

| Properties of Vacuum Gas Oil Distillate | |
|---|---|
| Viscosity (SUS) | 150 |
| Distillation, °F.(°C.) | |
| 1% | 653 (345) |
| 5% | 696 (369) |
| 50% | 784 (418) |
| 95% | 877 (469) |
| 99% | 915 (491) |
| Hydrogen, % | 13.40 |
| Nitrogen, ppm | 620 |
| Sulfur, % | 0.43 |
| Paraffins, % | 30.7 |
| Mononaphthenes, % | 16.9 |
| Polynaphthenes, % | 17.7 |
| Aromatics, % | 34.7 |
| KV 40° C., cs | 26.45 |
| KV 100° C., cs | 4.805 |
| Pour Point, °F.(°C.) | 95 (35) |
| Cloud Point, °F.(°C.) | 112 (44) |
| Flash, COC, °F.(°C.) | 421 (216) |
| Reaction conditions were as follows: | |
| LHSV, hr$^{-1}$ | 0.4 to 0.6 |
| Temperature, °F.(°C.) | 670 to 750 (350–400) |
| Pressure, psig (kPa) | 1400 to 1500 (9750–10440) |
| H$_2$ circulation | 3000 to 5000 scf H$_2$/BBL (534 to 890 Nm$^3$H$_2$/m$^3$) |

Prior to contacting with the vacuum gas oil, both catalyst compositions were presulfided with a mixture of 2% H$_2$S in H$_2$ at 240–380 kPa (20 to 40 psig.) The presulfiding procedure involved increasing the temperature from 200° to 400° C. (400° F. to 750° F.) over the course of four hours.

The compositions of the 343° C+ (650° F.+) fractions resulting from the hydrocracking of the VGO over the first and second hydrocracking catalyst compositions are shown in Table IX as follows:

TABLE IX

| | Hydrocracking of VGO Over Catalyst of Invention | | | | |
|---|---|---|---|---|---|
| Conversion, wt. % | Feed | 44 | 63 | 76 | 82 |
| Analysis of 343° C.+ Fraction | | | | | |
| Paraffins | 30.7 | 27.6 | 35.9 | 34.4 | 34.4 |
| Naphthenes | 34.6 | 56.0 | 51.6 | 55.2 | 51.4 |
| Aromatics | 34.7 | 16.4 | 12.5 | 10.4 | 14.2 |
| | Hydrocracking of VGO Over Zeolite Beta Catalyst | | | | |
| Conversion, wt. % | Feed | 44 | 54 | 67 | 87 |
| Analysis of 343° C.+ Fraction | | | | | |
| Paraffins | 30.7 | 34.0 | 29.1 | 17.3 | 10.3 |
| Naphthenes | 34.6 | 55.6 | 59.3 | 61.9 | 67.3 |
| Aromatics | 34.7 | 10.4 | 11.6 | 20.8 | 22.4 |

Figure 2:
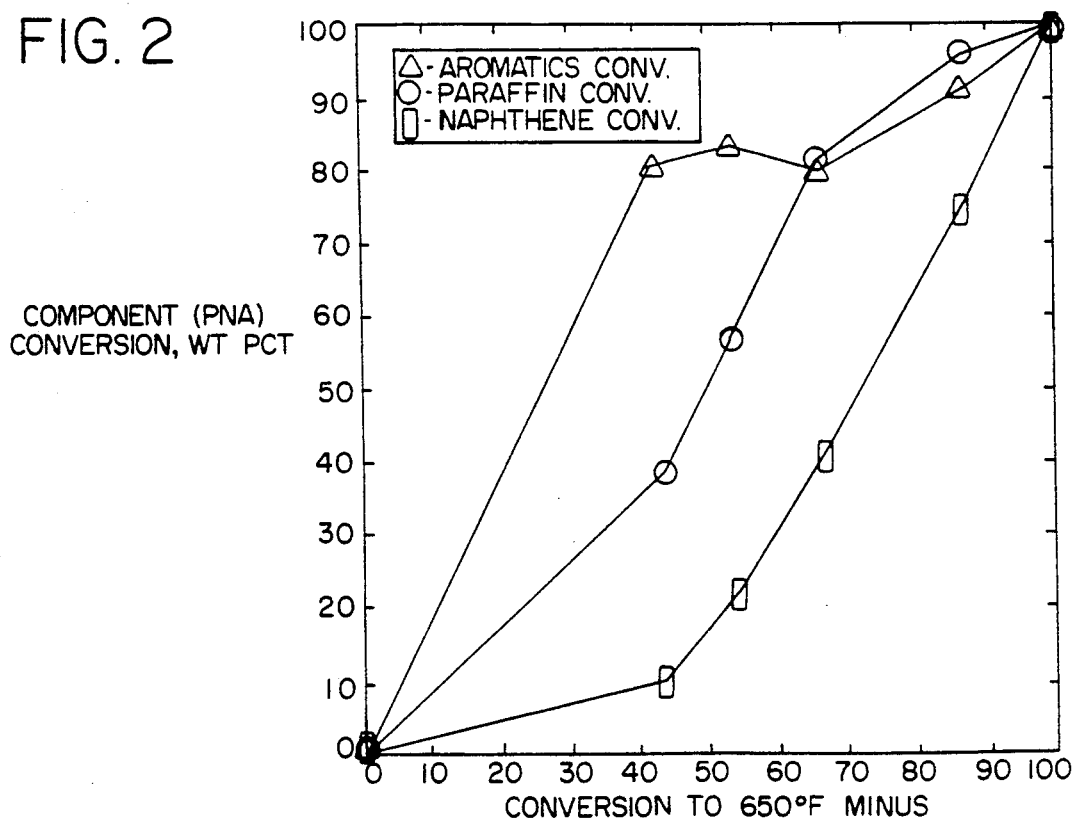
FIG. 2 is a graphical representation of process performance data relating to a catalytic hydrocracking process over NiW/zeolite Beta/ As$_2$O$_3$ catalyst.

The data in Table IX show that the hydrocracking catalyst composition of the invention selectively converts aromatics and concentrates paraffins and naphthenes in the heavy fraction. The zeolite Beta-based hydrocracking catalyst composition, by contrast, primarily converts paraffins while concentrating aromatics. This can also be seen by examining the compositional reaction pathways as shown in FIGS. 1 and 2. These two Figures compare the relative conversions of the paraffin, naphthene, and aromatic fractions in the 343° C.+ fraction versus overall conversion to 343° C.− for both catalysts. Above 50 wt. % conversion, the zeolite beta hydrocracking catalyst composition catalyst is more selective for paraffins conversion and less selective for aromatics conversion. The opposite is true of the first hydrocracking catalyst composition of the invention.

EXAMPLE 18

A sample of the zeolite produced as in Example 15 was used to produce a nickel and tungsten-containing catalyst composition for use in the single stage hydrocracking/dewaxing process of Example 20, infra. Initially, the zeolite (65 wt %) was mulled with Kaiser SA alumina (35 wt. %) and the resultant mixture was extruded with sufficient added water to provide a 1.6 mm (1/16 inch) diameter extrudate and the extrudate was dried at 120° C. (250° F.). The dried extrudate was then heated at 3° C. (5° F.)/minute to 480° C. (900° F.) in flowing nitrogen; held at 480° C. (900° F.) for 3 hours in flowing nitrogen; and held at 480° C. (900° F.) for 1 hour in a 50/50 volume ratio of air/nitrogen. The extrudate was then heated to 540° C. (1000° F.) at 3° C. (5° F.)/minute in the 50/50 air nitrogen/mixture, and held at 540° C. (1000° F.) for 3 hours.

The catalyst composition thus prepared was found to have the following physical properties (Table X):

TABLE X

| Alpha Value | 213 |
|---|---|
| Sodium, ppm | 630 |
| Density, g/cc | |
| Packed | 0.48 |
| Particle | 0.82 |
| Real | 2.57 |
| Pore Volume, cc/g | 0.83 |
| Surface Area, m$^2$/g | 451 |
| Pore Diameter, Angstroms | 74 |
| Crush, lb/in$^2$ (kg/m$^2$) | 77 (5.4 × 10$^4$) |

The final catalyst composition was prepared by first contacting the zeolite/Al$_2$O$_3$ product with 100% steam for 12 hours at 480° C. (900° F.). The resulting steamed composition was dried for 2 hours at 120° C. (250° F.) and was found to have an alpha value of 30.

The dried composition was then impregnated to incipient wetness at room temperature with a solution of 0.154 g/g of (NH$_4$)$_6$W$_{12}$O$_{39}$.9H$_2$O, dried in air at room temperature for 4 hours, then dried at 120° C. (250° F.) overnight.

The dried composition was then calcined in flowing dry air at 19° C. (34° F.)/minute to 540° C. (1000° F.), and held at this temperature for 3 hours in the flowing dry air.

The resulting composition was then impregnated to incipient wetness at room temperature with a solution of 0.206 g/g of Ni(NO$_3$)$_2$.6H$_2$O, dried in air at room temperature for 4 hours, then dried at 120° C. (250° F.) overnight.

The dried composition was then calcined in flowing dry air at 19° C. (34° F.)/minute to 540° C. (1000° F.) and held at this temperature for 3 hours in the flowing air. The final composition contained 3.3 wt % Ni and 8.6 wt % W.

EXAMPLE 19

A nickel and tungsten-containing alumina-bound USY catalyst composition was prepared for comparison with the nickel and tungsten-containing catalyst composition of Example 15 for catalyzing the hydrocracking/dewaxing process illustrated in Example 20, infra.

The USY catalyst composition was prepared by mixing 65 wt% USY zeolite with 35 wt % alumina, extruding, exchanging with NH₄NO₃ solution, steaming with 540° C. (1000° F.) steam for 10 hours and co-impregnating with a solution containing nickel and tungsten salts.

The final USY catalyst composition contained 2.0 wt % Ni and 6.0 wt % W.

EXAMPLE 20

The catalysts prepared according to Examples 18 and 19 were used simultaneously to hydrocrack/dewax separate samples of the vacuum gas oil employed in Example 17. In each case conversion was carried out at a pressure of 9690 kPa (1400 psig), a temperature of 354°-418° C. (670°-785° F.), and LHSV of 0.5-1.0 and a hydrogen circulation rate of 710-1600 Nm³/m³ (4000-9000 scf/bbl).

At 75% conversion, the product yield results were as presented in Table XI below. All material balances were between 90-100% recovery, mostly greater than 95%.

TABLE XI

Product Yields at 75% Conversion

| Catalyst | 166-343° C. (330-650° F.) Distillate, wt. % | C₅-166° C. (C₅-330° F.) Naptha, wt. % | C₁-C₄, wt. % |
|---|---|---|---|
| (Example 18) | 25 | 36 | 14 |
| (Example 19) | 33 | 37 | 5 |

Figure 3:
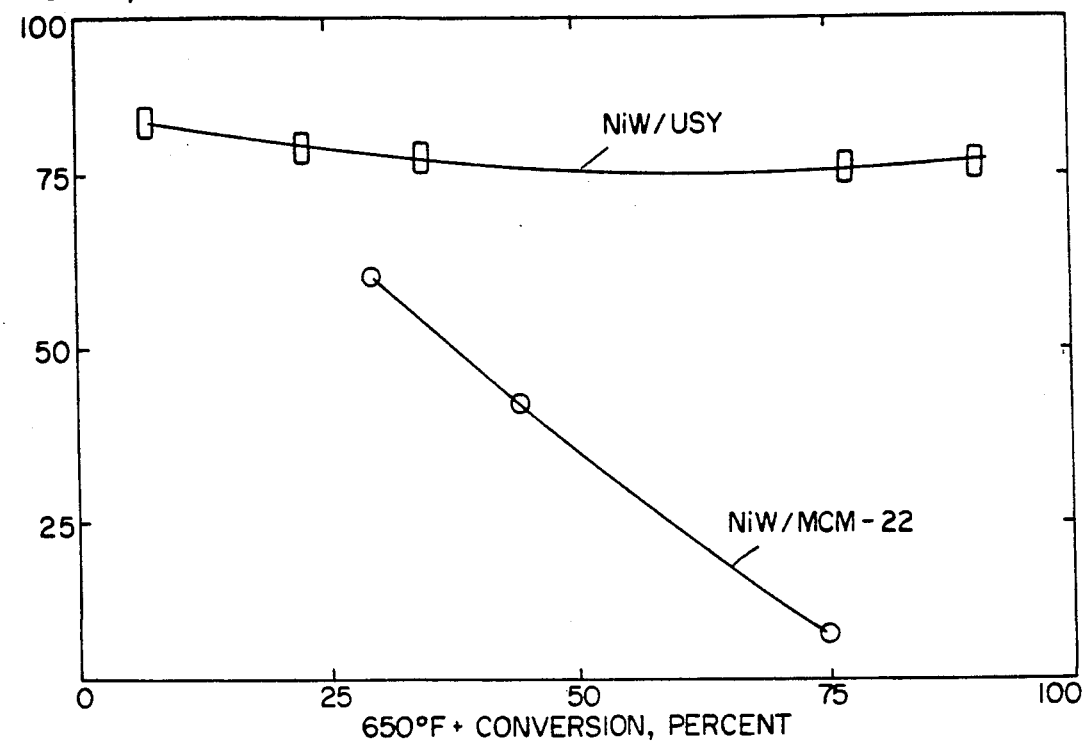
FIGS. 3 and 4 are graphical comparisons of process performance data relating to catalytic hydrocracking/dewaxing processes employing NiW/MCM-22, NiW/USY and NiW/zeolite Beta catalysts.

FIG. 3 shows measured pour points of the product at different conversions during the process over each catalyst. The plotted data show that hydrocracking/dewaxing over the zeolite of the invention provides a product having significantly lower pour point for a given rate of conversion.

EXAMPLE 21

This example provides a comparison between the catalyst composition of Example 18 (invention) and the Beta catalyst composition of Example 16 for the conversion of the heavy gas oil employed in Example 20.

Presulfiding of the catalysts was accomplished with a mixture of 2% H₂S in H₂ mixture at 240-380 kPa (20-40 psig) with a temperature increase of 200°-400° C. (400°-750° F.) over a period of 4 hours. Reaction conditions were varied over the following ranges:

| | |
|---|---|
| Temperature: | 670 to 750° F. (350-400° C.) |
| Pressure: | 1400 to 1500 psig (9750-10440 kPa) |
| LHSV: | 0.4 to 0.6 |
| H₂ Circulation: | 3000 to 5000 scf/bbl (530-890 Nm³/m³) |

The reported conversions are based on the 343° C.+ (650° F.+) portion of the feed. The results of the conversion employing the catalyst of the invention (Example 18) are set forth in Table XII and employing the zeolite beta catalyst of Example 16 are set forth in Table XIII as follows:

TABLE XII

| Conversion, % | 28 | 44 | 63 | 76 | 82 |
|---|---|---|---|---|---|
| Pour point, Herzog, °F.(°C.) | 62 (22) | 43 (6) | 47 (8) | 10 (−12) | 37 (3) |
| Pour point, °F.(°C.) | 65(18) | — | 55(13) | — | — |
| Cloud point, °F.(°C.) | 76(24) | — | 74(23) | — | — |
| KV at 40° C., cs | 27.17 | — | 21.91 | — | — |
| KV at 100° C., cs | 4.799 | — | 4.328 | — | — |
| VI | 94.0 | — | 103.9 | — | — |
| Hydrogen, wt. % | 13.78 | 13.99 | 14.11 | 14.20 | — |
| Nitrogen, ppm | 28 | 8 | 3 | 9 | 12 |
| Sulfur, wt. % | 0.01 | 0 | 0.01 | 0.002 | 0.002 |
| Paraffins, wt. % | 27.6 | 27.6 | 35.9 | 34.4 | 34.4 |
| Naphthenes, wt. % | 52.0 | 56.0 | 51.6 | 55.2 | 51.4 |
| Aromatics, wt. % | 20.4 | 16.4 | 12.5 | 10.4 | 14.2 |
| Simulated Distillation, °F. | | | | | |
| 5% | 683 | 686 | 685 | 685 | 703 |
| 50% | 774 | 772 | 766 | 764 | 771 |
| 95% | 868 | 867 | 861 | 859 | 863 |

TABLE XIII

| Conversion, % | 44 | 54 | 67 | 88 |
|---|---|---|---|---|
| Pour point, Herzog, °F. | 66(19) | 5(−15) | −47(−44) | −24(−31) |
| Pour point, °F.(°C.) | 65(18) | 25(−4) | −40(−40) | — |
| Cloud point, °F.(°C.) | 80(27) | 44(7) | −65(18) | — |
| KV at 40° C., cs | 27.72 | 34.96 | 51.31 | — |
| KV at 100° C., cs | 4.928 | 5.395 | 6.219 | — |
| VI | 100.5 | 82.3 | 49.1 | — |
| Hydrogen, wt. % | 13.93 | 13.89 | — | — |
| Nitrogen, ppm | 2 | 1 | — | — |
| Sulfur, wt. % | 0.01 | 0.01 | — | — |
| Paraffins, wt. % | 34.0 | 29.1 | 17.3 | 10.3 |
| Naphthenes, wt. % | 55.6 | 59.3 | 61.9 | 67.3 |
| Aromatics, wt. % | 10.4 | 11.6 | 20.8 | 22.4 |
| Simulated Distillation, °F. | | | | |
| 5% | 702 | 697 | 679 | 693 |
| 50% | 774 | 777 | 768 | 786 |
| 95% | 862 | 866 | 857 | 857 |

Figure 4:
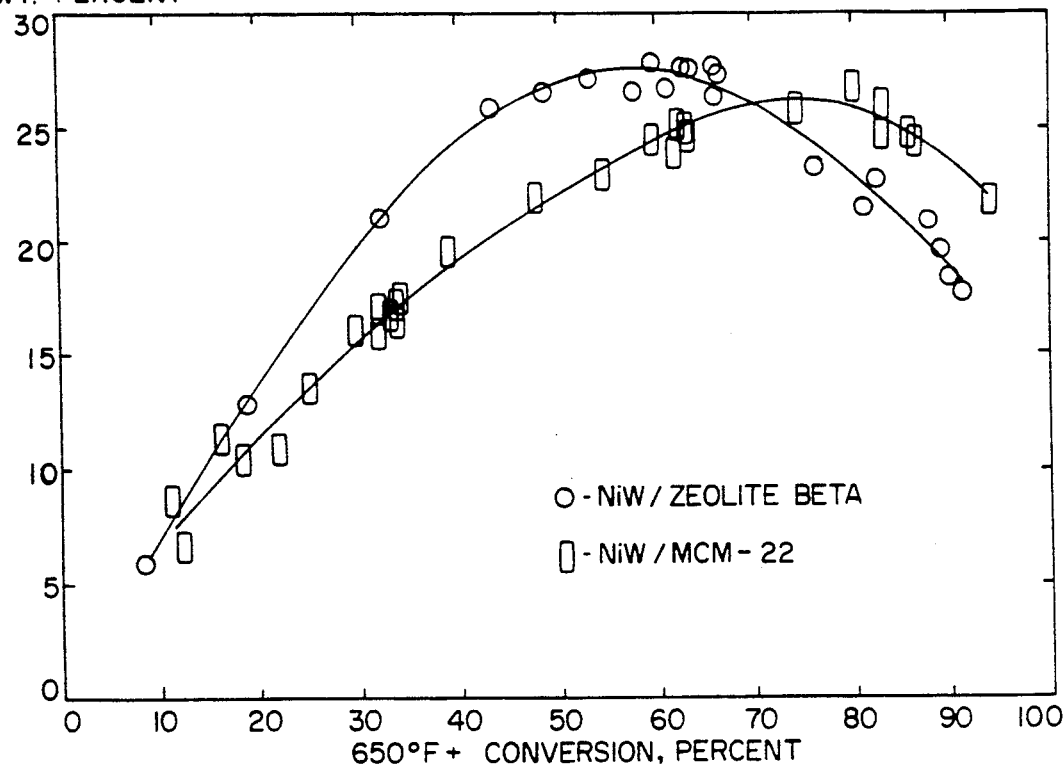

As shown in Tables XII and XIII, although catalyst compositions achieve pour point reduction, at conversions below 50%, where the catalyst of the invention makes less distillate and more gas than zeolite Beta, the former lowers the pour point to a greater extend (see FIG. 4). At higher conversion levels, zeolite Beta catalyst is superior in this regard. However, the low paraffin/high aromatic content of the zeolite beta producs at high conversion levels results in these products having low viscosity indexes.

The activity of the catalyst compositions including the zeolite of the invention and zeolite beta were compared at 60% conversion of the heavy gas oil of Table VIII (Example 17). At conditions of 9960 kPa (1430 psig), 0.54 LHSV and 800 Nm³/m³ (4500 scf H₂/bbl) feed, the temperature required to achieve 60% conversion was 377° C. (711° F.) for zeolite Beta and 383° C. (721° F.) for zeolite of the invention. FIG. 4 plots the distillate yield obtained with the two catalysts as a function of conversion. Both zeolite catalysts produced about the same maximum amount of distillate, but the maximum for zeolite of the invention occured at a significantly higher conversion level. Above 70% conversion, zeolite of the invention provides significantly better selectivity than that of the zeolite Beta.

However, when employed in combination, the differences in catalytic properties of the zeolite of the invention and zeolite Beta for the simultaneous hydrocracking and dewaxing of a heavy hydrocarbon feed complement each other and make it possible to improve the viscosity of the product while simultaneously achieving a low pour point.

What is claimed is:

1. A hydrocracking process comprising the step of contacting a hydrocarbon stream under hydrocracking conditions and in the presence of hydrogen with a hydrocracking catalyst composition comprising a synthetic porous crystalline zeolite having an X-ray diffraction pattern including lines set forth in Table I of the specification, is obtained 2. The process of claim 1 wherein the synthetic porous crystalline zeolite has an X-ray diffraction pattern including lines set forth in Table II of the specification.

3. The process of claim 1 wherein the synthetic porous crystalline zeolite has an X-ray diffraction pattern including lines set forth in Table III of the specification.

4. The process of claim 1 wherein the zeolite has equilibrium adsorption capacities of greater than 4.5 wt.% for cyclohexane vapor and greater than 10 wt.% for n-hexane vapor.

5. The process of claim 1 wherein the synthetic porous crystalline material has a composition comprising the molar relationship $$X_2O_3:(n)YO_2,$$

wherein n is at least 10, X is a trivalent element and Y is a tetravalent element.

6. The process of claim 5 wherein X comprises aluminum and Y comprises silicon.

7. The process of claim 1 wherein said hydrocracking catalyst composition also comprises a hydrogenation component.

8. The process of claim 1 wherein said hydrocracking conditions include a temperature of 260° C. to 450° C., a pressure of 2860 to 27680 kPa, an LHSV of 0.1 to 10 hr$^{-1}$, and a hydrogen circulation rate of 180 to 1780 Nm$^3$/m$^3$.

9. The process of claim 1 including the step of subjecting the hydrocarbon stream to hydrocracking with a hydrocracking catalyst composition comprising a larger pore molecular sieve and a hydrogenation component.

10. The process of claim 9 wherein said larger pore molecular sieve is zeolite Beta.

11. A dual stage hydrocracking conversion process which comprises:
(a) contacting a hydrocarbon stream boiling above a temperature of about 300° F. in a first stage under hydrocracking conditions and in the presence of hydrogen with a first hydrocracking catalyst composition comprising (i) a synthetic porous crystalline material characterized by an X-ray diffraction pattern including values substantially as set forth in Table I of the specification and (ii) at least one hydrogentaion component to provide a first hydrocracked effluent; and
(b) contacting said first hydrocracked effluent in a second stage under hydrocracking conditions and in the presence of hydrogen with a second hydrocracking catalyst composition comprising (i) zeolite Beta and (ii) at least one hydrogenation component to provide a second hydrocracked effluent.

12. The process of claim 11 wherein the first-stage synthetic porous crystalline material has a composition comprising the molar relationship $$X_2O_3:(n)YO_2,$$

wherein n is at least about 10, X is a trivalent element and Y is a tetravalent element.

13. The process of claim 11 wherein the first-stage synthetic porous crystalline material possesses equilibrium adsorption capacities of greater than about 4.5 wt. % for cyclohexane vapor and greater than about 10 wt. % for n-hexane vapor.

14. The process of claim 12 wherein X is selected from the group consisting of aluminum, boron, Fe, gallium and combinations thereof and Y is selected from the group consisting of silicon, germanium and combinations thereof.

15. The process of claim 12 wherein X comprises aluminum and Y comprises silicon.

16. The process of claim 1 wherein said synthetic porous crystalline material has been thermally treated at a temperature up to about 925° C. in the presence or absence of steam.

17. The process of claim 11 wherein said first-stage synthetic porous crystalline material has been thermally treated at a temperature up to about 925° C. in the presence or absence of steam.

18. A process for reducing the pour point of a waxy component-containing hydrocarbon oil feed which comprises contacting said feed with a catalyst composition under conditions suitable to effect hydrocracking and dewaxing of said feed to provide a hydrocracked/dewaxed product of reduced pour point, said catalyst composition comprising a synthetic porous crystalline material characterized by an X-ray diffraction pattern including values substantially as set forth in Table I of the specification.

19. The process of claim 18 wherein the synthetic porous crystalline material has a composition comprising the molar relationship $$X_2O_3:(n)YO_2,$$

wherein n is at least about 10, X is a trivalent element and Y is a tetravalent element.

20. The process of claim 18 wherein the synthetic porous crystalline material possesses equilibrium adsorption capacities of greater than about 4.5 wt. % for cyclohexane vapor and greater than about 10 wt. % for n-hexane vapor.

21. The process of claim 19 wherein X is selected from the group consisting of aluminum, boron, Fe gallium and combinations thereof and Y is selected from the group consisting of silicon, germanium and combinations thereof.

22. The process of claim 19 wherein X comprises aluminum and Y comprises silicon.

23. The process of claim 18 wherein said synthetic porous crystalline material has been thermally treated at a temperature up to about 925° C. in the presence or absence of steam.

24. The process of claim 18 wherein the catalyst composition further comprises at least one other zeolite.

25. The process of claim 18 wherein the catalyst composition further comprises zeolite Beta.

* * * * *

UNITED STATES PATENT AND TRADEMARK OFFICE
CERTIFICATE OF CORRECTION

PATENT NO. : 5,013,422

DATED : May 7, 1991

INVENTOR(S) : R.P.L. Absil et al.

It is certified that error appears in the above-identified patent and that said Letters Patent is hereby corrected as shown below:

Col. 3, line 34, "belwo" should be --below--
Col. 23, claim 1, line 4, "specification, is obtained" should be --specification wherein a hydrocracked product is obtained.--
Col. 23, claim 9, line 33, insert --further--before "sub-"
Col. 23, claim 9, line 34, "hydrocarbon stream" should be --hydrocracked product--
Col. 23, claim 9, line 36, after "sieve" insert --as compared to said porous crystalline zeolite,--
Col. 24, claim 14, line 10, "Fe," should be --iron,--
Col. 24, claim 21, line 48, "Fe" should be --iron,--

Signed and Sealed this

Third Day of September, 1991

Attest:

HARRY F. MANBECK, JR.

Attesting Officer

Commissioner of Patents and Trademarks